US010016269B2

(12) United States Patent
Spenciner et al.

(10) Patent No.: US 10,016,269 B2
(45) Date of Patent: Jul. 10, 2018

(54) FLIPPING-TYPE GRAFT FIXATION DEVICE AND METHOD

(71) Applicant: DePuy Mitek, LLC, Raynham, MA (US)

(72) Inventors: David B. Spenciner, North Attleboro, MA (US); Benjamin Chan, Oronoco, MN (US)

(73) Assignee: DEPUY MITEK, LLC, Raynham, MA (US)

( * ) Notice: Subject to any disclaimer, the term of this patent is extended or adjusted under 35 U.S.C. 154(b) by 1 day.

(21) Appl. No.: 15/262,175

(22) Filed: Sep. 12, 2016

(65) Prior Publication Data
US 2016/0374796 A1 Dec. 29, 2016

Related U.S. Application Data

(60) Division of application No. 14/024,728, filed on Sep. 12, 2013, now Pat. No. 9,456,892, which is a continuation of application No. 13/364,435, filed on Feb. 2, 2012, now Pat. No. 8,545,558.

(51) Int. Cl.
*A61F 2/08* (2006.01)

(52) U.S. Cl.
CPC ..... *A61F 2/0811* (2013.01); *A61F 2002/0852* (2013.01); *A61F 2002/0882* (2013.01); *A61F 2220/0016* (2013.01)

(58) Field of Classification Search
CPC ........ A61F 2/08; A61F 2/0805; A61F 2/0811; A61F 2002/0847; A61F 2002/0864; A61F 2002/0876; A61F 2002/0852; A61F 2002/0882; A61F 2220/0016
See application file for complete search history.

(56) References Cited

U.S. PATENT DOCUMENTS

| 5,306,301 | A | * | 4/1994 | Graf ................... A61B 17/0401 606/151 |
| 5,645,588 | A | | 7/1997 | Graf |
| 5,769,894 | A | | 6/1998 | Ferragamo |
| 6,086,591 | A | | 7/2000 | Bojarski |

(Continued)

FOREIGN PATENT DOCUMENTS

| EP | 2191791 A2 | 6/2010 |
| FR | 2926456 A1 | 7/2009 |

(Continued)

OTHER PUBLICATIONS

Rose Seavey, Sterilization of Surgical Implants: Did You Know, Education & Training, Nov. 2006, pp. 78-95.

*Primary Examiner* — Christopher D Prone
*Assistant Examiner* — Rokhaya Diop

(57) ABSTRACT

A buckle useful for cortical fixation has a graft retention loop slidably affixed thereto for movement from a first position adjacent a first end of the buckle to a second position at about the midpoint of the buckle. The buckle, with a graft over the loop, is drawn up lengthwise through a bone tunnel through a tibia and then flipped sideways to rest against the surface of the bone with the loop and graft depending back into the tunnel. The sliding attachment of the loop permits flipping of the buckle minimizes the flipping distance, which is the excess amount of the loop which must be pulled free of the tunnel to allow the buckle to be flipped sideways.

24 Claims, 8 Drawing Sheets

(56) References Cited

U.S. PATENT DOCUMENTS

| | | |
|---|---|---|
| 6,352,603 B1 | 3/2002 | Bryant |
| 6,902,573 B2 | 6/2005 | Strobel |
| 7,530,990 B2 | 5/2009 | Perriello et al. |
| 7,566,339 B2 | 7/2009 | Fallin |
| 7,594,923 B2 | 9/2009 | Fallin |
| 7,806,909 B2 | 10/2010 | Fallin |
| 8,545,558 B2 | 10/2013 | Spenciner |
| 8,834,523 B2 | 9/2014 | Ferragamo |
| 2007/0233241 A1 | 10/2007 | Graf et al. |
| 2009/0234396 A1 | 9/2009 | Medoff |
| 2010/0305585 A1 | 12/2010 | Fallin |
| 2010/0318126 A1 | 12/2010 | Fallin |
| 2011/0112640 A1 | 5/2011 | Amis et al. |
| 2013/0085526 A1* | 4/2013 | Graf ..................... A61F 2/0811 606/232 |
| 2013/0085527 A1* | 4/2013 | Ferragamo ............ A61F 2/0811 606/232 |
| 2013/0116787 A1 | 5/2013 | Ferragamo |
| 2013/0204366 A1 | 8/2013 | Spenciner |
| 2014/0018917 A1 | 1/2014 | Spenciner |

FOREIGN PATENT DOCUMENTS

| | | |
|---|---|---|
| GB | 2288739 A | 11/1995 |
| JP | 10-127672 | 5/1998 |
| JP | 2004-528121 | 12/2005 |
| JP | 2002-535077 | 3/2007 |
| JP | 2009-530061 | 8/2009 |
| WO | WO 2013049445 A1 | 4/2013 |
| WO | WO 2013049453 A1 | 4/2013 |

\* cited by examiner

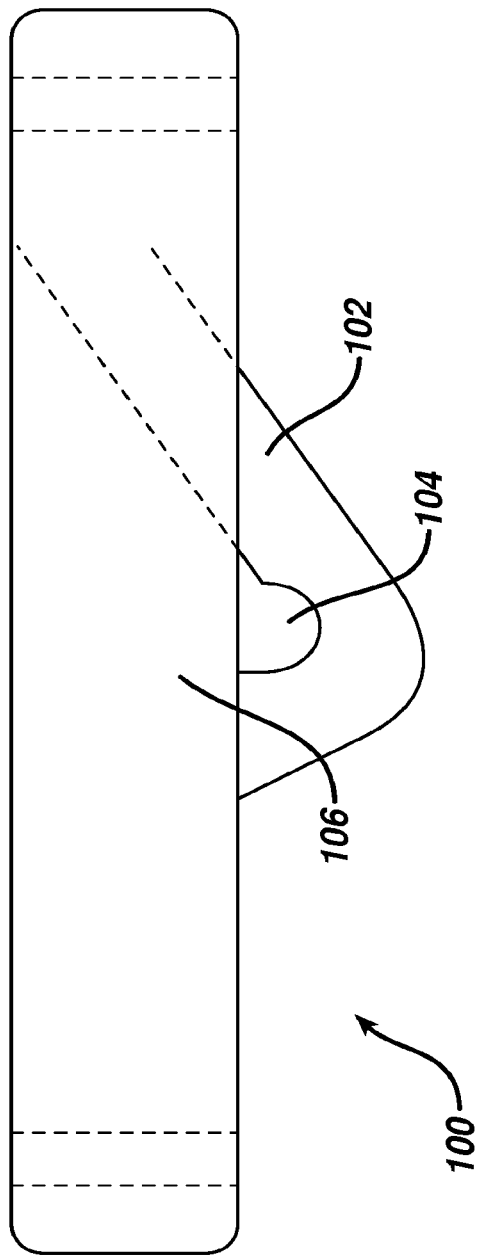

FLIPPING-TYPE GRAFT FIXATION DEVICE AND METHOD

CROSS REFERENCE TO RELATED APPLICATIONS

This application is a divisional application of U.S. patent application Ser. No. 14/024,728, entitled FLIPPING-TYPE GRAFT FIXATION DEVICE AND METHOD, filed Sep. 12, 2013 which is a continuation application of U.S. patent application Ser. No. 13/364,435, entitled FLIPPING-TYPE GRAFT FIXATION DEVICE AND METHOD, filed Feb. 2, 2012, now U.S. Pat. No. 8,545,558 which is incorporated herein by reference.

BACKGROUND

This application relates to graft fixation, and more particularly to graft tissue fixation employing flipping-type fixation devices.

Flipping-type fixation devices, such as disclosed in U.S. Pat. Nos. 5,306,301 and 5,645,588 incorporated herein by reference, allow a simple procedure to be used for fixing tissue such as in an Anterior Cruciate Ligament (ACL) reconstruction. Such device comprises an elongated bar having a central suture loop depending therefrom. A tunnel is prepared in the femur from a position at or near the patellar surface up through a portion of the femur and exiting through the side of the femur at a superior location. A graft is looped over the loop attached to the elongated bar. The bar is able to pass in one direction up through the tunnel. After exiting the superior end of the tunnel, the bar is flipped approximately 90 degrees so that it will not pass back through the tunnel and is positioned against the femur with the loop and graft hanging down into the tunnel therefrom. Tension on the graft keeps the bar in place against the bone surface.

To initiate the flipping, however, the bar must be passed completely outside of the tunnel. When it is then placed down against the bone the suture loop falls back into the tunnel by the amount that it was pulled free of the tunnel, about 50% of the length of the bar. This decreases the contact of the graft with the bone in the tunnel. Also, longer loop lengths have the potential to increase motion of the graft within the tunnel, thus potentially slowing the healing process in which the graft attaches to the bone.

SUMMARY OF THE INVENTION

The present invention overcomes these and other limitations of the prior art in a simple and elegant design.

A method according to the present invention provides for fixing a graft ligament into a bone tunnel. The method comprises the steps of: a) forming a graft construct by draping the graft ligament over a loop depending from a fixation buckle, the buckle having a length along a longitudinal axis which is at least twice a maximum lateral dimension, the tunnel having an exit where it exits the bone and the length also being larger than a maximum width of exit; b) pulling the graft construct up through the bone tunnel with the buckle traveling lengthwise through the tunnel with the loop depending from the buckle from a first position located below a midpoint of the length of the buckle; c) pulling the buckle out of the tunnel through the exit and rotating it so that its longitudinal axis is sufficiently out of alignment with the tunnel to prevent the buckle from passing back into the tunnel; d) moving the loop from the first position to a second position along the buckle, the second position being at about the midpoint of the buckle; and e) engaging the buckle against the bone at the exit with the loop depending into the tunnel from the second position on the buckle.

Preferably, the loop is received through at least one elongated slot on the buckle and moves from the first position to the second position by sliding along the at least one elongated slot. Preferably, the at least one slot has an end at about the midpoint of the buckle and the loop is engages with the end of the slot as it is moved into the second position.

Preferably, the loop slides along a surface of the buckle between the first position and the second position and that surface slopes downwardly as it approaches the midpoint of the buckle.

After step e) the loop depends into the tunnel by a first length and preferably, during step c) the loop depends into the tunnel by a second length that is less than the first length. While performing of step c) the second length is never less than the first length by more than 3.5 mm.

In one aspect of the invention, the graft ligament is an ACL replacement and the bone tunnel is formed through a tibia.

A graft retention device according to the present invention comprises an elongated body having a first end and a second end and a midpoint therebetween. A graft retention loop slidably affixes to the elongated body for movement along the elongated body from a first position adjacent the first end and a second position at about the midpoint. A stop on the elongated body prevents the loop from sliding past the second position toward the second end.

In one aspect of the invention, a leading line releasably attaches to the elongated body at its second end. Further, a trailing line may be releasably attached to the elongated body at its first end.

Preferably, the elongated body comprises a pair of elongated slots extending from adjacent the first end to about the midpoint and which define a tang therebetween, the loop passing through the slots and over the tang. In one aspect of the invention, the elongated bar has an upper surface, the tang has an upper surface and the upper surface of the tang slopes downwardly away from the upper surface of the buckle as the tang approaches the midpoint.

Preferably, the elongated body and the loop are sterile and formed from biocompatible implantable materials.

Preferably, the second position is located within a central 25% of a length of the elongated bar between its first end and its second end.

In one aspect of the invention, a retainer on the elongated body discourages movement of the loop out of the second position. The retainer can comprise one or more barbs.

A graft retention device according to the present invention comprises an elongated body having a first end and a second end. A graft retention loop slidably affixes to the elongated body for movement along the elongated body from a first position adjacent the first end and a second position at about the midpoint. The loop depends downwardly from the elongated body and is from the first position to the second position along a sliding surface. The sliding surface is lower at the second position than at the first position whereby to encourage the loop to move toward the second position.

In one aspect of the invention, a leading line releasably attaches to the elongated body at its second end. A trailing line can releasably attach to the elongated body at its first end.

Preferably, the elongated body and the loop are sterile and formed from biocompatible implantable materials.

Preferably, the elongated body comprises a pair of elongated slots extending from adjacent the first end to about the midpoint and which define a tang therebetween, the loop passing through the slots and over the tang, the tang forming the sliding surface.

In one aspect of the invention, a retainer on the elongated body discourages movement of the loop out of the second position. The retainer can comprise one or more barbs. The retainer can comprise a narrowing of the tang between the slots at the midpoint. The retainer can comprise a hollow in the upper surface of the tang defined at least in part by a transition which transition restricts sliding of the loop out of the hollow.

Preferably, the graft retention device has a flipping distance of no greater than 3.5 mm and more preferably no greater than 2 mm. Preferably, the graft retention device has a flipping distance no greater than 1/3 of a maximum length of the body and more preferably no greater than 1/4 of the maximum length.

BRIEF DESCRIPTION OF THE DRAWINGS

FIG. 7 is a side elevation view of an alternative embodiment of a buckle according to the present invention, having a hollow for capturing the loop at the midpoint;

DETAILED DESCRIPTION

Figure 1:
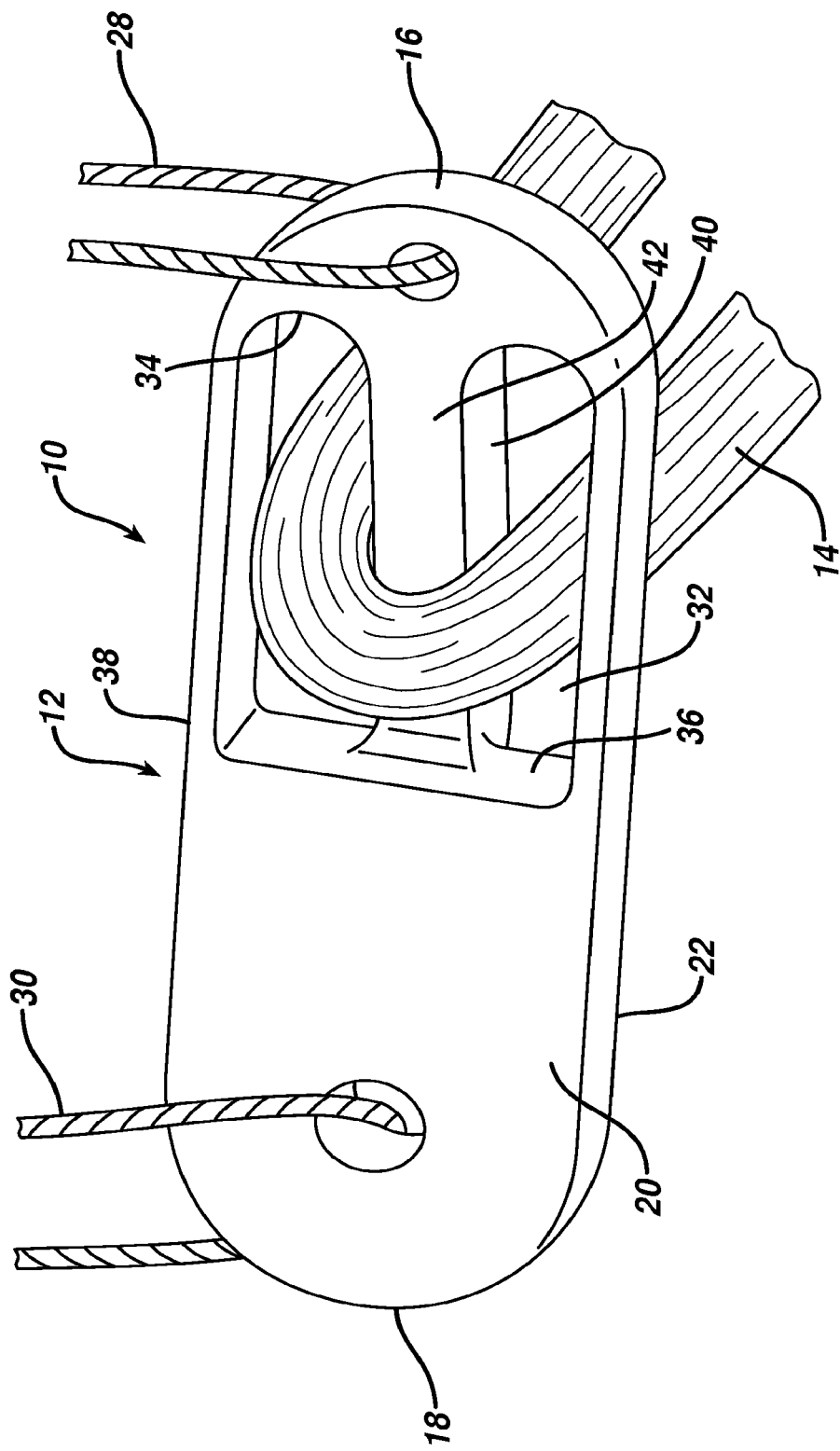
FIG. 1 is a perspective view of a fixation device buckle according to the present invention.
Figure 2:
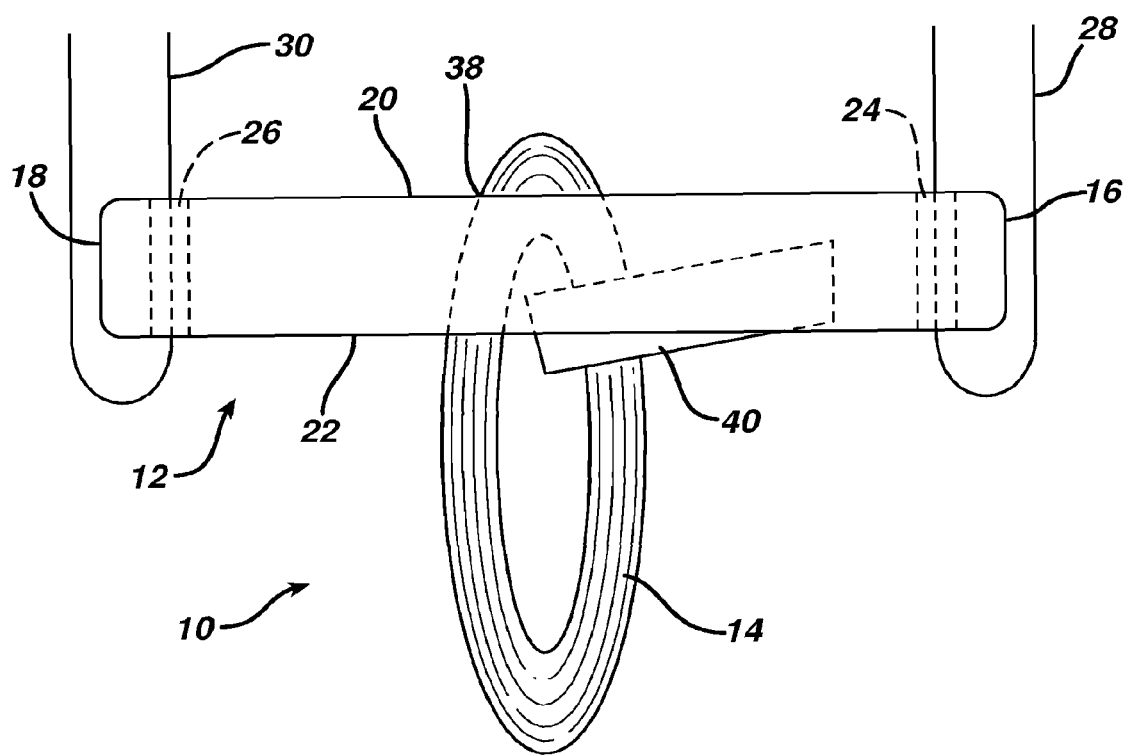
FIG. 2 is a side elevation view of a fixation device according to the present invention employing the buckle of FIG. 1.

FIGS. 1 and 2 show an illustrative embodiment of a graft fixation device 10 according to the present invention. It comprises an elongated bar or buckle 12 having a graft receiving loop 14 depending therefrom. The buckle 12 comprises a first end 16 and second end 18, and an upper surface 20 and lower surface 22. (The terms "upper" and "lower" and related terms such as "upwards" are used herein with reference to the surfaces of the buckle 12 just defined, with the lower surface 22 being that surface which will face a bone—not shown in FIGS. 1 and 2—when the buckle 12 is employed.) First and second holes 24 and 26 penetrate the buckle 12 at the first and second ends 16 and 18 respectively, passing from the upper surface 20 to the lower surface 22. The first hole 24 receives a trailing line 28 and the second hole 26 a leading line 30. The trailing line 28 and leading line 30 are preferably formed of ORTHOCORD #2 suture available from Ethicon, Inc. of Somerville, N.J. The leading line 30 may experience higher stress than the trailing line 28 while placing the fixation device 10 as will become apparent as the placement procedure is described. The second hole 26 is shown slightly larger than the first hole 24 (although they could be made the same size) and the leading line 30 can be a higher strength suture such as with a larger diameter than the trailing line 28. This difference can be used to differentiate the leading line 30 and trailing line 28. They can also be differentiated in some other fashion such as via varying colors or visual patterns.

A pair of longitudinal slots 32 penetrate the buckle 12 from the upper surface 20 to the lower surface 22 and extend from a first end 34 adjacent the first hole 24 to a second end 36 at a midpoint 38 of the buckle 12. The slots 32 define a retention tang 40 therebetween. An upper surface 42 of the retention tang slopes downwardly from the first end 34 of the slots 32 to the second end 36 to encourage the loop 14 to migrate toward the midpoint 38 at implantation. The loop 14 is threaded through the slots 32 and slides along the retention tang upper surface 42. Preferably, the vertical dimension of the retention tang 40, as viewed in FIG. 2, is constant from the first end 34 to second end 36 to enhance its strength and rigidity, with the retention tang 40 thus depending slightly below the buckle lower surface 22 at the midpoint 38. The tang 40 is shown with a slope below the upper surface 20 of 13.6 degrees but could be anywhere from zero to about 45 degrees. It could also vary in slope, such as getting progressively steeper toward the midpoint 38 to encourage the loop to stay at the midpoint 38 after implantation.

Preferably, for an ACL repair the buckle 12 is approximately 12 mm long, 4 mm wide and 1.5 to 2.5 mm thick, with the thickest portion being the midpoint 38 where the tang 40 depends. The tang 40 is approximately 1.5 mm thick. The buckle 12 is preferably formed of a biocompatible material such as 6Al-4V Ti alloy. Preferably, the loop 14 is woven of ultra-high molecular weight polyethylene, such as DYNEEMA, and polyester. The material of the loop 14 is preferably about 2 mm in diameter, preferably being in a range of from #2-0 up through about 4 mm, and the loop 14 is preferably between about 8 mm and 60 mm long. The loop 14 can be woven onto the buckle 12 to form a continuous loop without knots. U.S. Pat. No. 6,352,603 to Bryant, incorporated herein by reference, illustrates one method for achieving such a construct.

Figure 3:
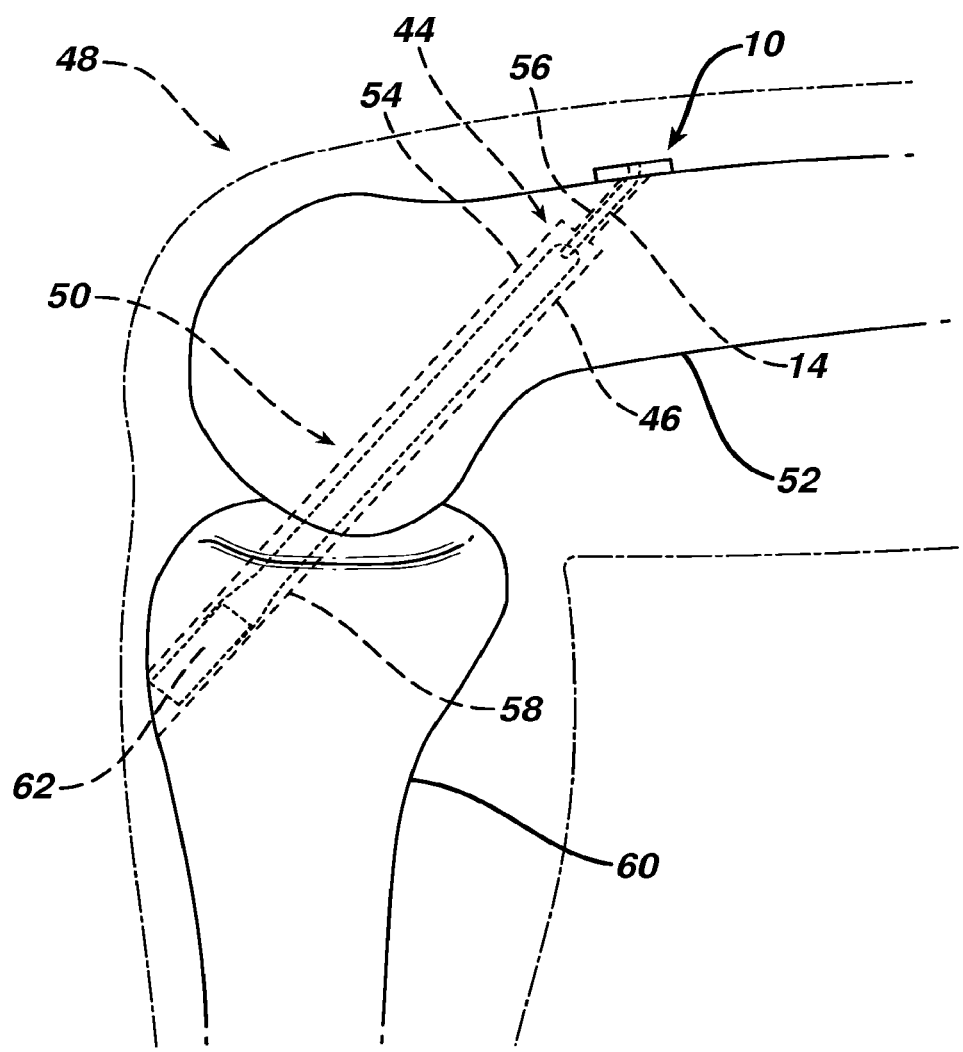
FIG. 3 is a side elevation view in cross-section of a ACL repair in a knee employing the fixation device of FIG. 2.

FIG. 3 illustrates a graft construct 44, comprising a tissue graft 46 looped over the loop 14 of the fixation device 10, in place in a patient's leg 48. A tunnel 50 in the leg's femur 52 comprises a larger diameter inferior portion or socket 54 sized to accommodate the graft 46 and a smaller diameter superior portion or passing channel 56 sized to accept the buckle 12 in a lengthwise orientation. The buckle 12 sits against the femur 52 in a sideways orientation with the loop 14 depending down through the passing channel 56 and into the socket 54 in which is placed the graft 46. An opposite end of the graft 46 is placed into a tibial tunnel 58 in the leg's tibia 60 and held in place with an anchor 62 such as the INTRAFIX® anchor available from DePuy Mitek Inc. of Raynham, Mass.

Figure 4A:
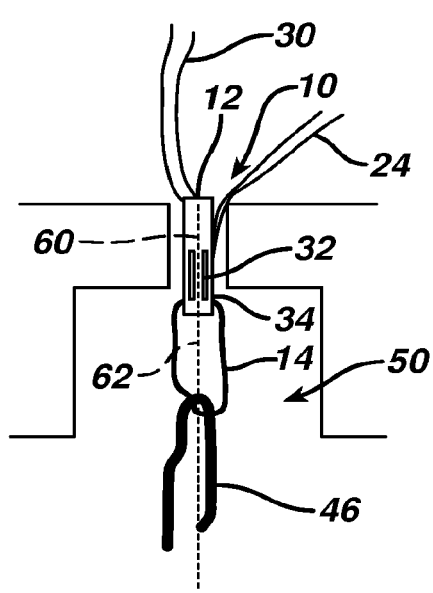
FIGS. 4A to 4D are side elevation views in cross-section of an ACL repair procedure employing the fixation device of FIG. 2.
Figure 4B:
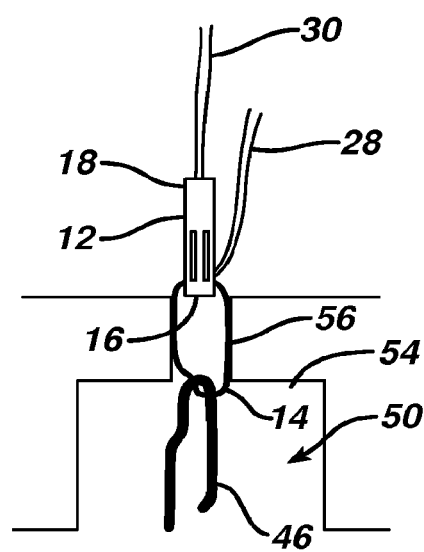

FIGS. 4A to 4D illustrate the process of passing the buckle 12 up through the tunnel 50. At the start of the procedure, the graft tissue 46 is threaded through the loop 14. A longitudinal axis 60 of the buckle 12 is oriented coaxially with a longitudinal axis 62 of the tunnel 50, with the loop 14 depending from the first end 34 of the slots 32 (FIG. 4A). Tension on the leading line 30 pulls the second end 18 of the buckle 12 upwardly out of the tunnel 50 until the first end 16 is free of the tunnel (FIG. 4B). Preferably, the loop 14 and the passing channel 56 are dimensioned so that if the graft construct 44 is pulled up until the graft tissue 46 abuts the end of the socket 54 the first end 16 of the buckle 12 has just cleared the end of the tunnel 50 thus providing tactile feedback to the surgeon that the buckle 12 is properly positioned to be rotated.

Figure 4C:
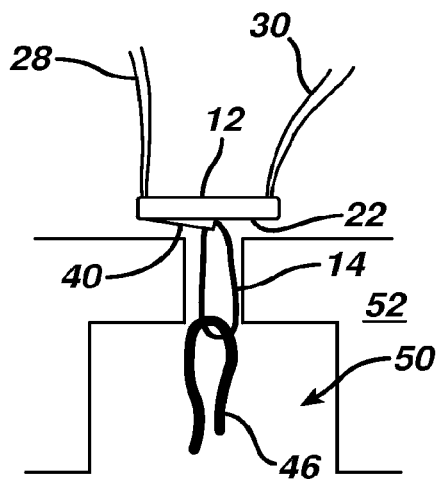
Figure 4D:
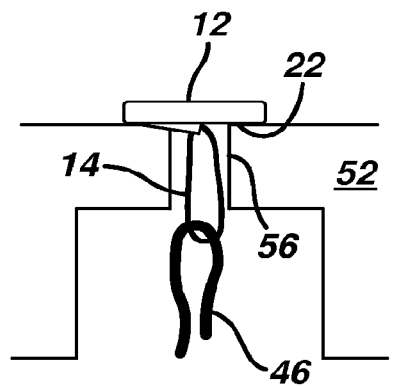

Rotation is approximately 90 degrees and can occur by applying tension to the trailing line 28 (FIG. 4C). The final orientation depends upon the angle at which the tunnel 50 penetrates the femur 52. As the buckle 12 is rotated, opposing tension supplied by the graft tissue 46 tends to cause the loop 14 to slide along the retention tang 40 leaving it depending down into the tunnel 50 from the midpoint 38 of the buckle 12. This occurs with a distinct snapping motion that can be felt by the surgeon through the trailing line 28 to provide tactile feedback that the migration has occurred properly. The trailing line 28 and leading line 30 are then removed and tension from the graft tissue 46 pulls the buckle 12 lower surface 22 firmly against the femur 52 (FIG. 4D). The crosswise orientation of the buckle 12 versus the tunnel 50 and the loop 14 depending from the midpoint 38 of the buckle 12 prevent the buckle from migrating back into the tunnel 50 thus providing secure fixation of the graft tissue 46.

The slope of the tang upper surface 42 assists in urging the loop 14 toward the midpoint 38. Its angle on the femur 52 versus the tunnel 50 also tends to pull the loop 14 across the buckle 12 to sit at the slot second ends 36 and the buckle 12. Locating the ends 36 at the midpoint 38 thus helps keep the loop 14 seated at the midpoint 38. In terms of final seating of the loop 14 the term "midpoint" can be broadly construed. Seating at the exact middle of the buckle 12 provides an equal amount of buckle to each side thereof to minimize any chance that the buckle 12 can slip along the bone in such a fashion that and end thereof could fall back into the tunnel 50. In practical terms the loop 14 can be seated in other locations yet still be safely situated to prevent the buckle 12 from falling back into the tunnel 50. Preferably, the loop 14 is seated somewhere in the middle 50% of the length of the buckle 12 and more preferably within the middle 25%.

Example 1

The gap which exists between the graft 46 and the end of the socket 54 can be reduced by the present invention. To evaluate this advantage similarly sized buckles were compared. Buckle A was a commercially available product similar to that described in the '301 Patent and Buckle B is the buckle 12 depicted in FIG. 1 herein. Each was 12.2 mm long, 4.0 mm wide, and 1.4 mm thick, with Buckle B being 2.5 mm thick at its midpoint due to the bottom of the tang depending below the lower surface. The buckles were threaded with loops of similar thickness and construction to each other; with the tests performed using loop lengths of between 15 and 30 mm. Caliper measurements were performed of the loop from the buckle to the furthest inside portion of the loop in two configurations: 1) the loop stretched downwardly from and perpendicular to the buckle as representative of the final fixation position, and 2) the loop stretched from the trailing end of the buckle and parallel to the buckle as representative of the position as the buckle is being pulled up through the tunnel immediately prior to being flipped. The differences in these measurements represent the flipping distance and for Buckle A were 6.6 mm. For Buckle B they were 3.2 mm. In a subsequent test employing a buckle design similar to that of FIGS. 5 and 6 the flipping distance was reduced to 2 mm.

The flipping distance is representative of the gap between the graft 46 and the end of the socket 54. Ideally this gap is zero and the graft 46 extends all the way to the end of the socket 54. Buckle B substantially reduced the flipping distance.

Figure 5:
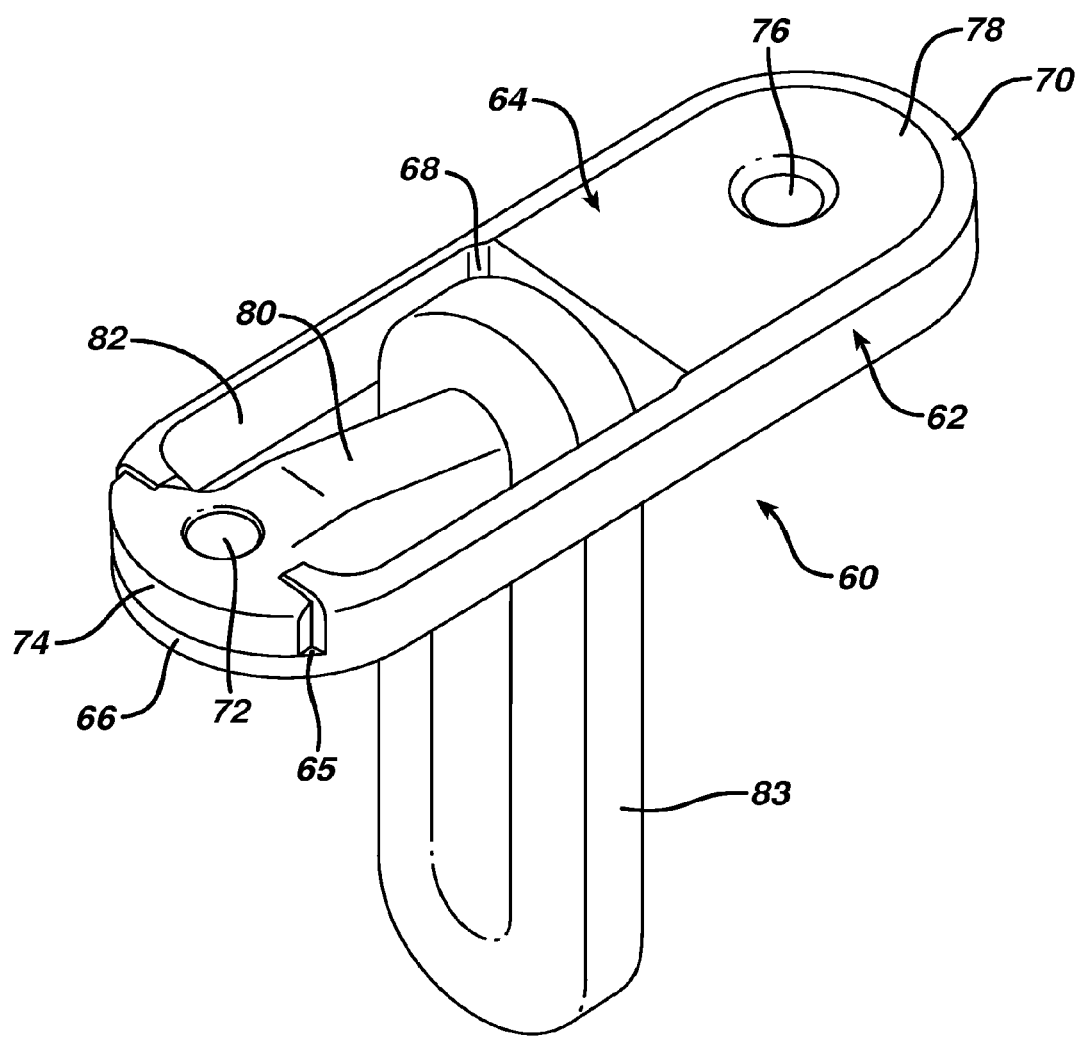
FIG. 5 is a top perspective view of an alternative embodiment of a buckle according to the present invention, showing the loop seated at the midpoint.
Figure 6:
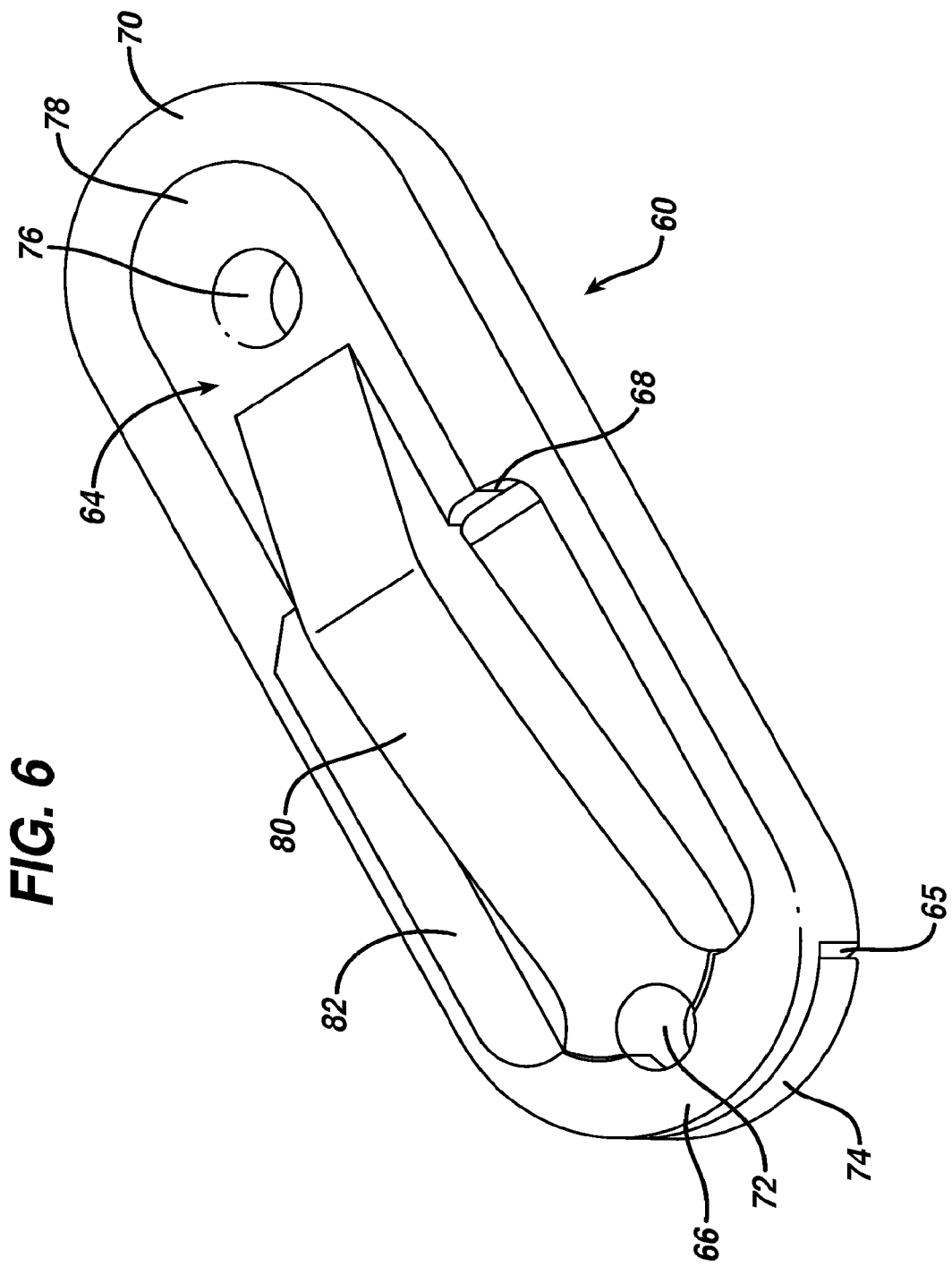
FIG. 6 is an underside perspective view of the buckle of FIG. 5, shown without the loop attached.

FIGS. 5 and 6 illustrate another fixation buckle 60 according to the present invention that incorporates a similar shape and function to the buckle 12, but further comprises a two-piece construction comprising an outer frame 62 and an insert 64. The frame 62 has a first flange 65 at a first end 66 and a second flange 68 at a second end 70. The insert 64 fits within the frame 62 and has rabbets 71 that mate with the flanges 65 and 68. The insert 64 incorporates a first hole 72 at a first end 74 and a second hole 76 at a second end 78 plus a retention tang 80. A sidewall 82 of the frame 62 can be slightly thinner adjacent the retention tang 80 to accommodate a loop 83 (not shown in FIG. 6).

The two-piece construction eases assembly. The fixation device 10 of FIG. 1 is preferably formed by weaving the loop 14 around the retention tang 40 to form the loop 14. This potentially complicates the weaving process. With the buckle 60, the loop 83 can be woven separately, and then threaded over the retention tang 80 prior to fitting the insert 64 into the frame 62. The insert 64 can be held in the frame 62 by a friction fit, an interference fit, by welding or other appropriate means. The interaction between the flanges 65 and 68 and the insert 62 provides structural integrity against forces applied downwardly upon the retention tang 80.

Refinements and variations to the buckle 12, and as well to the buckle 60, could include slots 32 which extend to both sides such that the second side mirrors the first, and the retention tang 40 sloping down from both ends toward the center. This would allow a surgeon to pull the buckle 12 up through the tunnel 50 by either end. Also, the upper surface 42 of the retention tang 40 could be rounded to provide a better surface for the loop 14 to ride over and lessen chafing of the loop 14.

Figure 8B:
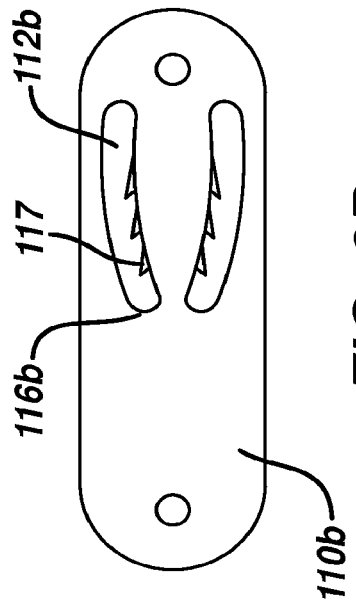
FIG. 8B is a top plan view of an alternative embodiment of a buckle according to the present invention having slots which get closer together toward the midpoint of the buckle.
Figure 8D:
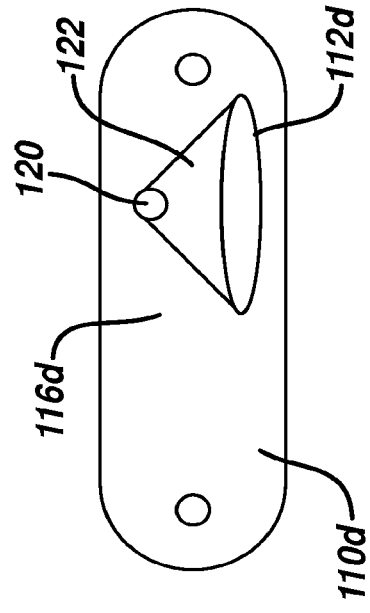
FIG. 8D is a top plan view of an alternative embodiment of a buckle according to the present invention having a single slot.
Figure 8A:
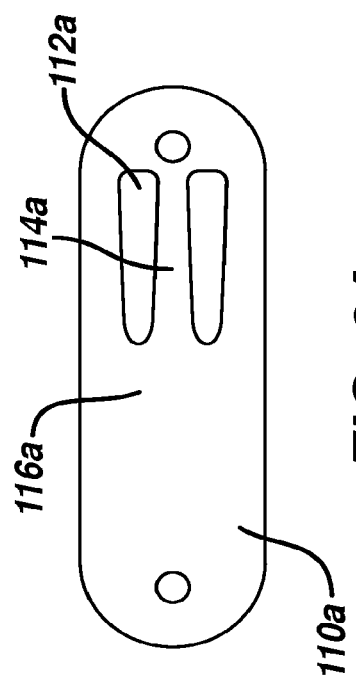
FIG. 8A is a top plan view of an alternative embodiment of a buckle according to the present invention having slots which narrow toward the midpoint of the buckle.
Figure 8C:
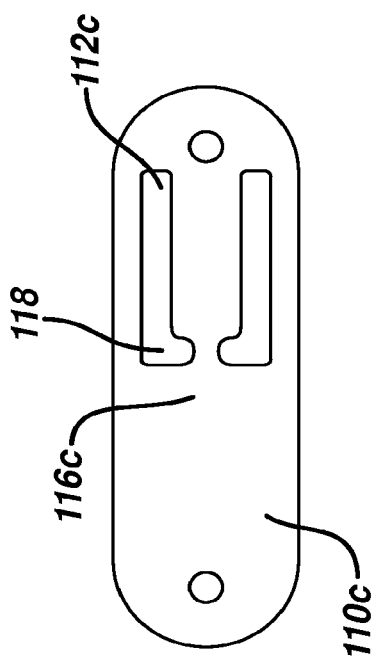
FIG. 8C is a top plan view of an alternative embodiment of a buckle according to the present invention having slots which turn inwardly towards each other at the midpoint of the buckle.

Provision can be made to discourage the loop 14 from moving away from the midpoint 38, such as by providing barbs (not shown) along the upper surface 42 or other areas of the buckle 12 where they may engage the loop 14 as it slides along the slots 32. FIG. 7 shows a buckle 100 having a tang 102 will a pronounced dip 104 to capture and retain the loop 14 at a midpoint 106. In FIGS. 8A to 8D like parts have like part numbers with a subscript corresponding the figure number. In FIG. 8A a buckle 110a has a pair of slots 112a which define a tang 114a sloping downwardly toward and terminating at a midpoint 116a. The slots 112a get narrower toward the midpoint 116a so as to pinch the loop 14 (not shown in FIGS. 8A to 8D) and hold it in place. FIG. 8B illustrates a buckle 110b in which the slots 112b get closer together towards the midpoint 116b. The tension on the loop 14 would encourage the loop 14 to close laterally and stay at the midpoint 116b. A series of barbs 117 are also shown which are intended to discourage the loop 14 to move away from the midpoint 116b. FIG. 8C works similarly, but the slots 112c have a sharp inward transition 118 at the midpoint 116c. In FIG. 8D rather than a pair of slots, there is one slot 112d and an aperture 120 through which the loop 14 would thread and thus only one portion of the loop 14 would slide along a surface 122 which slopes downwardly toward the midpoint 116d of the buckle 110d.

The configuration of slots 32 forming the tang 40 for attaching the loop 14 to the buckle and allowing its movement is preferred due to its simplicity, strength and economy of material in construction. However, other attachments techniques which allow movement of the loop from a position near the first end of the buckle 12 to a position near the midpoint of the buckle 12 are contemplated and within the scope of the present invention. The buckle is particularly suited to ACL repair, but can be useful in other repairs such as for example reattachment of a biceps brachii tendon.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A graft retention device comprising:
   an elongated body having a first end and a second end and a midpoint therebetween;
   a graft retention loop slidably affixed to the elongated body for movement along the elongated body from a first position adjacent the first end and a second position at about the midpoint;
   a stop on the elongated body which prevents the loop from sliding past the second position toward the second end;
   the elongated body comprising a pair of elongated slots which extend from adjacent the first end to about the midpoint and which define a tang therebetween, the loop passing through the slots and over the tang; and
   the elongated body having an upper surface and the tang having an upper surface, the upper surface of the tang sloping downwardly away from the upper surface of the elongated body as the tang approaches the midpoint.

2. The graft retention device of claim 1 and further comprising a leading line releasably attached to the elongated body at its second end.

3. The graft retention device of claim 1 and further comprising a trailing line releasably attached to the elongated body at its first end.

4. The graft retention device of claim 1 wherein the elongated body and the loop are sterile and formed from biocompatible implantable materials.

5. The graft retention device of claim 1 wherein the second position is located within a central 25% of a length of the elongated bar between its first end and its second end.

6. The graft retention device of claim 1 wherein the elongated body has a lower surface, opposite its upper surface, and wherein the pair of elongated slots penetrate the body from the upper surface to the lower surface.

7. The graft retention device of claim 1 and further comprising a retainer on the elongated body which discourages movement of the loop out of the second position.

8. The graft retention device of claim 7 wherein the retainer comprises one or more barbs.

9. The graft retention device of claim 1 having a flipping distance of no greater than 3.5 mm.

10. The graft retention device of claim 9 having a flipping distance of no greater than 2 mm.

11. The graft retention device of claim 1 having a flipping distance of no greater than 1/3 of a maximum length of the body between its first end and its second end.

12. The graft retention device of claim 11 having a flipping distance of no greater than 1/4 of the maximum length of the body.

13. A graft retention device comprising:
    an elongated body having a first end and a second end;
    a graft retention loop slidably affixed to the elongated body for movement along the elongated body from a first position adjacent the first end and a second position at about the midpoint;
    the loop depending downwardly from the elongated body and being slidable from the first position to the second position along a sliding surface, the sliding surface being lower at the second position than at the first position whereby to encourage the loop to move toward the second position; and
    the elongated body comprising a pair of elongated slots extending from adjacent the first end to about a midpoint between the first end and the second end, and which define a tang therebetween, the loop passing through the slots and over the tang, the tang forming the sliding surface.

14. The graft retention device of claim 13 and further comprising a leading line releasably attached to the elongated body at its second end.

15. The graft retention device of claim 13 and further comprising a trailing line releasably attached to the elongated body at its first end.

16. The graft retention device of claim 13 wherein the elongated body and the loop are sterile and formed from biocompatible implantable materials.

17. The graft retention device of claim 13 and further comprising a retainer on the elongated body which discourages movement of the loop out of the second position.

18. The graft retention device of claim 17 wherein the retainer comprises one or more barbs.

19. The graft retention device of claim 17 wherein the retainer comprises a narrowing of the tang between the slots at the midpoint.

20. The graft retention device of claim 17 wherein the retainer comprises a hollow in the upper surface of the tang at least partially defined by a transition therewith.

21. The graft retention device of claim 13 having a flipping distance of no greater than 3.5 mm.

22. The graft retention device of claim 21 having a flipping distance of no greater than 2 mm.

23. The graft retention device of claim 13 having a flipping distance of no greater than 1/3 of a maximum length of the body between its first end and its second end.

24. The graft retention device of claim 23 having a flipping distance of no greater than 1/4 of the maximum length of the body.

* * * * *